(12) United States Patent
Tomza

(10) Patent No.: US 10,415,181 B2
(45) Date of Patent: Sep. 17, 2019

(54) KNIT FABRIC FOR ORTHOPEDIC SUPPORT MATERIAL

(71) Applicant: 3M INNOVATIVE PROPERTIES COMPANY, St. Paul, MN (US)

(72) Inventor: Pawel A. Tomza, Wroclaw (PL)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 986 days.

(21) Appl. No.: 14/783,182

(22) PCT Filed: Apr. 10, 2014

(86) PCT No.: PCT/US2014/033670
§ 371 (c)(1),
(2) Date: Oct. 8, 2015

(87) PCT Pub. No.: WO2014/169136
PCT Pub. Date: Oct. 16, 2014

(65) Prior Publication Data
US 2016/0053433 A1    Feb. 25, 2016

(30) Foreign Application Priority Data

Apr. 12, 2013  (EP) ..................................... 13001924

(51) Int. Cl.
| | | |
|---|---|---|
| *D04B 21/16* | (2006.01) | |
| *D04B 21/18* | (2006.01) | |
| *D06N 3/14* | (2006.01) | |
| *D06N 3/00* | (2006.01) | |
| *A61F 13/04* | (2006.01) | |
| *D04B 21/20* | (2006.01) | |
| *A61F 5/058* | (2006.01) | |

(52) U.S. Cl.
CPC ........... *D06N 3/0009* (2013.01); *A61F 5/058* (2013.01); *A61F 13/041* (2013.01); *D04B 21/16* (2013.01); *D04B 21/18* (2013.01); *D04B 21/207* (2013.01); *D06N 3/14* (2013.01); *D10B 2331/042* (2013.01); *D10B 2509/028* (2013.01)

(58) Field of Classification Search
USPC ........................................................ 428/369
See application file for complete search history.

(56) References Cited

U.S. PATENT DOCUMENTS

| | | | |
|---|---|---|---|
| 3,630,194 A | | 12/1971 | Boardman |
| 3,908,644 A | | 9/1975 | Neinart et al. |
| 3,932,526 A | | 1/1976 | Koshar |
| 4,411,262 A | | 10/1983 | von Bonin et al. |
| 4,427,002 A | | 1/1984 | Baron et al. |
| 4,433,680 A | | 2/1984 | Yoon |
| 4,467,594 A | * | 8/1984 | Eschenbach ............. D02G 1/20 28/271 |
| 4,502,479 A | | 5/1985 | Garwood et al. |
| 4,574,793 A | | 3/1986 | Lee et al. |
| 4,588,635 A | | 5/1986 | Donovan |
| 4,667,661 A | | 5/1987 | Scholz et al. |
| 5,405,643 A | | 4/1995 | Scholz |
| 5,498,232 A | | 3/1996 | Scholz |
| 5,512,354 A | | 4/1996 | Scholz et al. |
| 5,540,982 A | | 7/1996 | Scholz et al. |
| 6,159,877 A | * | 12/2000 | Scholz ................... D04B 21/14 428/902 |
| 6,981,955 B2 | | 1/2006 | Schultze et al. |

FOREIGN PATENT DOCUMENTS

| | | |
|---|---|---|
| EP | 0 407 056 | 1/1991 |
| EP | 0 680 300 | 11/1995 |
| EP | 0 680 527 | 11/1995 |
| WO | WO 1994/16745 | 8/1994 |

OTHER PUBLICATIONS

Complete Textile Glossary "Thread Definition". Celanese Acetate LLC. Charlotte NC. 2001 (Year: 2001).*
Tortora, Phyllis G., Fairchilds Dictionary of Textiles: 7th Edition. Fairchils Publications, New York. 2003. pp. 8, 287. (Year: 2003).*
Blaeser, E.J.; "A review of the technology and applications for microdenier polyester"; presented at TAPPI 1991 Nonwovens Conference; Tappi Journal; 1991; pp. 153-156.
Davies, S.; "Fine Micro Filaments—What is a Microfibre?"; Textile Horizons; vol. 8, No. 4; 1988; pp. 5 and 49-50.

* cited by examiner

*Primary Examiner* — Jenna L Johnson

(57) ABSTRACT

The invention relates to a knit fabric for orthopedic support material. The knit fabric comprises in the weft yarn in-lay/cross direction synthetic organic microdenier yarn of no greater than 1.5 denier per filament (dpf) and synthetic organic multi-filament yarn of greater than 2.5 denier per filament (dpf). It is impregnated with a curable resin which on activation with a curing agent forms a cast supporting the patient's limb. The knit fabric according to invention exhibits the high holding capacity of the resin over time, said capacity being sufficient to prevent resin leak from a resin-coated fabric.

12 Claims, No Drawings

KNIT FABRIC FOR ORTHOPEDIC SUPPORT MATERIAL

CROSS REFERENCE TO RELATED APPLICATIONS

This application is a national stage filing under 35 U.S.C. 371 of PCT/US2014/033670, filed Apr. 10, 2014, which claims priority to European Patent Application No. 13001924.3, filed Apr. 12, 2013, the disclosure of which is incorporated by reference in its/their entirety herein.

FIELD OF THE INVENTION

The present invention relates to knit fabrics. More specifically, the present invention relates to knit fabrics used as backings for orthopedic immobilization devices such as orthopedic casting tapes.

BACKGROUND OF THE INVENTION

Orthopedic immobilization or support materials, e.g., casting tapes, are composed of a fabric backing and a curable compound such as plaster-of-paris or a synthetic resinous material. The fabric used in the backing serves several important functions. For example, it provides a convenient means of delivering the curable compound. It also helps reinforce the final composite cast. Furthermore, for an orthopedic casting material that incorporates a curable resin, use of a backing material with numerous voids, i.e., a backing with an apertured configuration, ensures adequate porosity. This allows a sufficient amount of curing agent, such as water, to contact the resin and initiate cure. This also ensures that the finished cast is porous, breathable, and comfortable for the patient.

The fabric used in many of the backings of orthopedic casting materials on the market is often made of fiberglass. Such fiberglass backing materials generally provide casts with strength superior to casts that use synthetic organic fiber knits, gauze, nonwovens, and other nonfiberglass composite backings. Although fiberglass backing materials provide superior strength, they are of some concern to the medical practitioner during the removal of casts. Because casts are removed using conventional oscillatory cast saws, fiberglass dust is typically generated. Although the dust is generally classified as nonrespirable nuisance dust, and therefore not typically hazardous, many practitioners are concerned about the effect inhalation of such fiberglass dust particles may have on their health. Furthermore, although casts containing fiberglass generally have improved x-ray transparency compared to that of plaster-of-paris casts, the knit structure is visible, which can interfere with the ability to see fine detail in a fracture.

In developing backing materials for orthopedic casts, conformability of the material is an important consideration.

In order to provide a "glove-like" fit, the backing material should conform to the shape of the patient's limb receiving the cast. This can be especially difficult in areas of bony prominences such as the ankle, elbow, heel, and knee areas. The conformability of a material is determined in large part by the longitudinal extensibility, i.e. lengthwise stretch, of the fabric.

Conformable fiberglass backings have been developed, however, special knitting techniques and processing equipment are required. To avoid the need for special techniques and equipment, nonfiberglass backing materials have been developed to replace fiberglass. However, many of the commercially available nonfiberglass backings, such as those containing polyester or polypropylene, also have limited extensibility, and thus limited conformability.

The extensibility, and thereby conformability, of some fiberglass or polyester knit backing materials has been improved by incorporating elastic yarns into the wales of a chain stitch. The use of a backing that incorporates highly elastic yarns is not necessarily desirable, however, because of the possibility of causing constriction and further injury to the limb if the casting tape is not carefully applied.

The constriction results from a relatively high elastic rebound force. Thus, inelastic or only slightly elastic stretch is preferred. A second characteristic that can be a drawback of these backings is the tendency to wrinkle longitudinally when the backing is extended. This results in decreased conformability and a rough surface.

European patent EP 0 680 527 describes a fabric backing for orthopedic support materials. The backing constitutes a resin-coated sheet comprising an extensible knit fabric comprising different non-fiber glass yarn components coated with a curable resin wherein one of the yarn components is microdenier yarn of no greater than 1.5 denier and wherein the knit fabric has an extensibility of 15-100% measured after applying a load of 0.26 N per mm. The knit fabric is a warp knit fabric having a chain stitch, a weft in-lay and a weft insertion. The microdenier yarn is positioned in the fabric as a weft in-lay, and preferably is a polyester yarn. The fabric further comprises a stretch yarn positioned in chain stitch. Further it comprises nonfiberglass stiffness-controlling yarn, preferably monofilament yarn.

U.S. Pat. No. 6,159,877 discloses a modified fabric backing for orthopedic support materials. The backing constitutes a curable resin-coated sheet comprising a knit fabric comprising organic yarn of low modulus (5-10 g per denier) having a non-fiberglass stiffness controlling yarn knit into the fabric as weft insertions (of modulus greater than ca. 5 g per denier). Said stiffness controlling yarn comprises ca. 3-20% by weight of yarn in total and is a monofilament yarn of 80-350 denier. Also, the fabrics includes a stretch yarn.

The backing material is sufficiently conformable to patient's limb, has low potential for constriction, resist wrinkling during application and provides a cured cast exhibiting high strength, rigidity and porosity. Also, the backing is radiotranslucent (X-ray transparent).

The aim of the invention is to provide a conformable non-fiberglass backing material having above-listed characteristic, exhibiting high holding capacity of the resin over time and being sufficient to prevent resin leak from resin coated sheet.

SUMMARY OF THE INVENTION

The present invention provides backing materials for impregnation with a resin, i.e. resin-impregnated sheets. These resin-impregnated sheets are particularly useful as orthopedic support materials, i.e. medical dressings capable of hardening and immobilizing and/or supporting a body part.

Although referred to herein as resin-impregnated "sheets", such hardenable dressings can be used in tape, sheet, film, slab, or tubular form to prepare orthopedic casts, splints, braces, supports, protective shields, orthotics, and the like. Additionally, other constructions in prefabricated shapes can be used. As used herein, the terms "orthopedic support material," "orthopedic immobilization material," and "orthopedic casting material" are used interchangeably to encompass any of these forms of dressings, and "cast" or "support" is used to include any of these orthopedic structures.

Typically, the backing materials of the present invention are used in orthopedic casting tapes, i.e. rolls of fabric impregnated with a curable casting compound. The backing materials of the present invention provide thin casting tapes that are advantageously wrinkle-free during application. Furthermore, they provide superior conformability and moldability without excessive elasticity.

Thus, the present invention relates to a resin-coated sheet material comprising a knit fabric with a curable resin, said knit fabric comprising in the weft yarn in-lay/cross direction
 a synthetic organic microdenier yarn of no greater than 1.5 denier per filament (dpf) and
 a synthetic organic multi-filament yarn of greater than 2.5 denier per filament (dpf).

Preferably, the weight ratio of microdenier yarn to yarn in total is 10-30%. The preferred microdenier yarn is of 0.8-1.3 dpf and/or multi-filament yarn used in the weft is of 3.5-6 dpf. More preferably, the threads of multi-filament yarn used in the weft are not twisted.

Preferably the weight ratio of synthetic organic microdenier yarn to synthetic organic multi-filament yarn in the weft yarn is between 1:1.3 to 1:6. More preferably, the synthetic organic microdenier yarn and the synthetic organic multi-filament yarn are air jet intermingled.

Preferably, the synthetic organic microdenier yarn and/or synthetic organic multi-filament yarn are made of polyester. More preferably, the polyester is poly(ethylene terephthalate).

Preferably, the microdenier yarn and a mulifilament yarn are used in combination with a non-microdenier stretchable yarn. Said stretchable yarn is an synthetic organic yarn and is positioned in warp/machine direction. The weight ratio of synthetic organic non-microdenier stretchable yarn to yarn in total is 27-33%. More preferably, the synthetic organic stretchable yarn is made of polyester, most preferably of polyester comprising poly(ethylene terephthalate), poly(trimethylene terephthalate) or their combinations.

Preferably a curable resin is a water curable resin, especially an isocyanate functional prepolymer.

As stated to above, the resin-coated sheet material of the invention is used for preparation of an orthopedic support material, preferably for orthopedic casting tape or a casting splint.

DETAILED DESCRIPTION OF THE INVENTION

The present invention provides a resin-impregnated sheet material, preferably for use as a backing component of an orthopedic immobilization material such as a casting tape. The backing component acts as a reservoir for a curable casting compound, e.g. a resinous material, during storage and end-use application of the casting tape. That is, the fabric used to form the backing of an orthopedic support material, such as a casting tape, is impregnated with a curable resin such that the resin is thoroughly intermingled with the fabric fibers and within the spaces created by the network of fibers. Upon cure, the resin undergoes polymerization and curing leading to a thermoset state, i.e. a cross-linked state, creating a rigid structure.

The fabrics used in the orthopedic support materials of the present invention must have certain ideal textural characteristics, such as surface area, porosity, and thickness. Such textural characteristics effect the amount of resin the backing can hold and the rate and extent to which the curing agent, e.g. water, comes in contact with the bulk of the curable resin impregnated in the fabric. For example, if the curing agent is only capable of contacting the surface of the resin, the major portion of the resin would remain fluid for an extended period resulting in a very long set time and a weak cast. This situation can be avoided if the resin layer is kept thin. A thin resin layer, however, is typically balanced against the amount of resin applied to the fabric to attain sufficient rigidity and formation of sufficiently strong bonding between layers of tape. A thin resin layer can be achieved at appropriate resin loadings if the fabric has a relatively high surface-to-volume ratio in a porous structure.

The amount of curable casting compound delivered must be sufficient such that adequate layer to layer lamination is achieved. Because the modulus of elasticity for organic synthetic fabrics such as polyester is far lower than that for fiberglass, polyester backings provide little support to the cured composite. Thus, the polyester backing needs to hold a greater amount of resin per unit area in order to achieve fiberglass-like strength.

Typically, a cast consists of about 4-12 layers of overlapping wraps of tape, preferably about 4-5 layers in non-weight-bearing uses and 8-12 layers in weight-bearing areas such as the heel. Thus, a sufficient amount of curable resin needs to be applied in these few layers to achieve the desired ultimate cast strength and rigidity.

On the other hand the amount of curable casting compound delivered should not be too great in order to avoid a resin "pooling". The pooling phenomenon is an excessive resin leak under the force of gravity to the bottom of the roll of resin coated sheet material. Since the required resin holding level is high and the viscosity of the resin is temperature dependent, the pooling happens on ageing of the resin-coated sheet, for example during storage of the rolls of resin coated sheet material.

According to invention, the resin-coated sheet material is provided, which exhibits the required resin holding level and good lamination strength. The combination of both technical features results in resin-coated sheet material of ideal pooling characteristic. The detrimental resin leakage is not manifested even on a prolonged storing at an elevated temperature. The resin holding level is preferably as high as 55-70%, more preferably 58-67%.

These and other advantageous characteristics are imparted to the fabric through the use of a unique knit construction having a synthetic organic microdenier yarn in the fabric of the backing comprising in the weft yarn in-lay (cross) direction of no greater than 1.5 denier per filament and synthetic organic multifilament yarn of greater than 2.5 denier per filament. The threads composed of multifilament yarn of greater than 2.5 dpf preferably are not twisted.

Preferably, the synthetic organic microdenier yarn and a synthetic organic multifilament yarn are used in combination with a stretchable yarn, preferably a heat shrinkable yarn. The stretchable yarn is used in warp/machine direction.

The microdenier yarns can be made of any organic staple fiber or continuous filament of synthetic or natural origin. Suitable staple fibers and filaments for use in the microdenier yarn include, but are not limited to, polyester, polyamide, polyaramid, polyolefin, rayon, halogenated polyolefin, copolymers such as polyether esters, polyamide esters, as well as polymer blends. Preferably, the microdenier yarns are made of polyester fibers or filaments. Generally, this is because polyester yarns are relatively inexpensive, currently available, and regarded as relatively safe and environmentally friendly. Furthermore, polyester yarns do not require drying prior to coating with a water curable resin due to a low affinity for atmospheric moisture, and they have a high affinity for most resins. If desired dyed microdenier yarns can be used.

Microdenier yarn is combined with multi-filament yarn made from filaments of diameter larger than 2.5 denier. These larger diameter yarns is an organic synthetic yarn, for example larger polyester, polyamide, polyacrylonitrile, polyurethane, polyolefin, rayon yarns.

An organic stretchable yarn, such as elastic stretch yarn or thermoplastic stretch yarn, is used in warp/machine direction to impart extensibility. The stretchable yarn may be a microdenier yarn, but preferably the stretchable yarn is one of a higher denier than the microdenier yarn. i.e. of non-microdenier yarn. Preferably, yarn is prepared from fibers or filaments of greater than about 1.5 denier, more preferably of greater than 1.8 denier per filament, such as of about 2.0-2.5 denier, which compact the fabric to the desired extent. The stretchable yarn can be made of fibers or filaments of up to about 6.0 denier.

Upon shrinkage, the stretchable, heat shrinkable yarns used in the present invention are highly extensible, i.e. greater than about 40%. This results in a fabric that is highly extensible, i.e. greater than about 45-60%, without the use of highly elastic materials.

Suitable thermoplastic heat shrinkable yarns are made of polyester, polyamide, and polyacrylonitrile fibers or filaments. Preferred heat shrinkable yarns are made of polyester and polyamide fibers or filaments. More preferably, the heat shrinkable yarns are made of polyester fibers or filaments for the reasons listed above for the microdenier yarns.

The fabric may be heated by using sources such as hot air, steam, infrared (IR) radiation, liquid medium, or by other means as long as the fabric is heated to a high enough temperature to allow the shrinkage to occur, but not so high that the filaments or fibers melt. Steam at 10.3 newtons/cm$^2$ works well, but requires subsequent drying of the fabric. The preferred method for shrinking polyester heat shrinkable yarn uses hot air at a temperature of about 120-180° C., preferably at a temperature of about 140-160° C. The temperature required generally depends on the source of the heat, the type of heat shrinkable yarn, and the time the fabric is exposed to the heat source, e.g. web speed through a fixed length heating zone. Such a temperature can be readily determined by one of skill in the art.

The fabrics of the present invention can be coated with any curable resin system with which the yarns of the fabric do not substantially react. Preferably the resin is water curable. Water-curable resins include polyurethanes, cyanoacrylate esters, isocyanate functional prepolymers of the type described in U.S. Pat. No. 4,667,661. Other resin systems which can be used are described in U.S. Pat. Nos. 4,574,793, 4,502,479, 4,433,680, 4,427,002, 4,411,262, 3,932,526, 3,908,644 and 3,630,194. Preferably, the resin is that described in European Application EP 0407056.

Generally, a preferred resin is coated onto the fabric as a polyisocyanate prepolymer formed by the reaction of an isocyanate and a polyol. The isocyanate preferably is of a low volatility, such as diphenylmethane diisocyanate (MDI), rather than a more volatile material, such as toluene diisocyanate (TDI). Suitable isocyanates include 2,4-toluene diisocyanate, 2,6-toluene diisocyanate, mixtures of these isomers, 4,4'-diphenylmethane diisocyanate, 2,4' diphenylmethane diisocyanate, mixtures of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. Typical polyols for use in the prepolymer system include polypropylene ether glycols and/or polyethylene ether glycols and/or esters or ethers of these glycols. By using high molecular weight polyols, the rigidity of the cured resin can be reduced.

The reactivity of the resin once it is exposed to the water curing agent can be controlled by the use of a proper catalyst. The reactivity must not be so great that: (i) a hard film quickly, forms on the resin surface preventing further penetration of the water into the bulk of the resin; or (ii) the cast becomes rigid before the application and shaping is complete.

Foaming of the resin should be minimized since it reduces the porosity of the cast and its overall strength. Since foaming occurs due to liberation of carbon dioxide during reaction with isocyanate groups, the possible way to minimize foaming is the reduction of the concentration of isocyanate groups in the prepolymer.

However, to have reactivity, workability, and ultimate strength, an adequate concentration of isocyanate groups is necessary. Although foaming is less at low resin contents, adequate resin content is required for desirable cast characteristics such as strength and resistance to peeling. The most satisfactory method of minimizing foaming is to add a foam suppressor such as silicone antifoam, for example at a concentration of about 0.05 to 1.0 percent by weight.

The preferred polyurethane prepolymer resin is the chemical material of composition as presented in Table 1.

TABLE 1

| Chemical composition of polyurethane prepolymer resin | |
|---|---|
| Ingredient | Part by weight |
| 4,4'-Diphenylmethane diisocyanate-polypropylene glycol polymer | 50-70 |
| Diphenylmethane diisocyanate homopolymer | 6-10 |
| Diphenylmethane diisocyanate | 20-30 |
| Polyethylene glycol monooleyl ether | 5-10 |
| Dimorpholinodiethyl ether | <2 |
| BHT (antioxidant) | <0.5 |

The isocyanate equivalent weight of the resin is in the range of 367-377 and the viscosity is 37500-42000 cP.

The resin systems used with the fabrics of the present invention may contain fillers. Such fillers can be organic or inorganic. Preferably they are generally inorganic microfibers such as whiskers (highly crystalline small single crystal fibers) or somewhat less perfect crystalline fibers such as boron fibers, potassium titanate, calcium sulfate, and calcium metasilicate.

The resin is coated or impregnated into the fabric. The amount of resin used is best described on a filler-free basis, i.e. in terms of the amount of fluid organic resin excluding added fillers.

As a result of the fabric used in the backings of the present invention in combination with the preferred resin systems, the backings provide highly extensible orthopedic support materials, e.g. casting tapes, having an extensibility, strength, and durability equivalent to, or superior to, that of conventional fiberglass products. Furthermore, the backing fabrics, i.e. backing materials, of the present invention advantageously provide superior conformability and moldability, without excessive elasticity. Preferred fabrics of the present invention provide high resin holding capacity and coating uniformity. The unique combination of those features results in very low ability for detrimental pooling (leaking the resin off).

The preparation of the orthopedic casting materials of the present invention generally involves coating the curable resin onto the fabric by standard techniques. Manual or mechanical manipulation of the resin (such as by a nip roller or wiper blade) into the fabric is usually not necessary.

However, some manipulation of the resin into the fabric may sometimes be desirable to achieve proper impregnation. Care should be given not to stretch the fabric during resin coating, however, so as to preserve the stretchability of the material for its later application around the desired body part. The material is converted to 10-12 foot lengths and wound on a polyethylene core under low tension to preserve stretch. The roll is sealed in an aluminum foil pouch for storage.

Orthopedic casting materials prepared in accordance with the present invention are applied to humans or other animals in the same fashion as other known orthopedic casting materials. First, the body member or part to be immobilized is preferably covered with a conventional cast padding and/or stockinet to protect the body part. Generally, this is a protective sleeve of an air-permeable fabric such that air may pass through the sleeve and the cast to the surface of the skin. Preferably, this sleeve does not appreciably absorb water and permits the escape of perspiration. An example of such a substrate is a knitted or woven crystalline polypropylene material. Then, the curable resin is typically activated by dipping the orthopedic casting material in water or other aqueous solution. Excess water may then be squeezed out of the orthopedic casting material.

The material is wrapped or otherwise positioned around the body part so as to properly conform thereto. Preferably, the material is then molded and smoothed to form the best fit possible and to properly secure the body part in the desired position. Although often not necessary, if desired, the orthopedic casting materials can be held in place during cure by wrapping an elastic bandage or other securing means around the curing orthopedic casting material. When curing is complete, the body part is properly immobilized within the orthopedic cast or splint which is formed.

Preferred Embodiment

A preferred fabric for use in the casting tape backing of the present invention is a knit of the following construction:
polyester microdenier yarn used in the weft of 0.8 to 1.3 denier per filament,
polyester multi-filament yarn of 3.5-6 denier per filament used in the weft as a stiffness controlling yarn,
wherein the weight ratio of microdenier yarn to yarn in total is 10-30%,
wherein the threads composed of multi-filament yarn are not twisted,
wherein the weight ratio of synthetic organic microdenier yarn to synthetic organic multi-filament yarn in the weft yarn is between 1:1.3 to 1:6,
and polyester non-microdernier stretchable yarn used in warp in amount of 27-33% yarn in total.

The fabric made from this particularly preferred composition is heat shrunk by passing the fabric under a source of heat, such as a forced hot air gun, at an appropriate temperature (about 150° C.). The heat causes the fabric to shrink under essentially no tension. The fabric is annealed at 175° C.

The fabric is coated with water curable resin in amount to achieve 58-67% resin content. The preferred water curable resin is the standard ESCP resin of composition essentially as given in Table 1.

EXAMPLE 1

Polyester microdenier yarn used in weft is 167 dtex/144f/1, i.e. composed of filaments of 1.045 denier (1.16 dtex). The multi-filament yarn is Trevira 835 dtex/160f/5—not twisted—i.e. multi-filament yarn of filaments of 4.70 denier (5.22 dtex). Trevira 835 dtex/160f/5 is the stiffness controlling yarn. The ratio of microdenier threads to multi-filament threads in the weft is 1:5. The weight ratio of microdenier yarn to multi-filament yarn in the weft yarn is approximately 1:5. Both, microdenier yarn and multi-filament yarn are made of poly(ethylene terephthalate). The polyester microdenier yarn and polyester multi-filament yarn are air jet intermingled.

Polyester heat shrinkable, non-microdenier stretchable yarn used in the warp is 167 dtex/72f, i.e. composed of filaments of 2.09 denier (2.32 dtex). The stretchable yarn is made of poly(ethylene terephthalate) and poly(trimethylene terephthalate).

The weight ratio of polyester microdenier yarn to yarn in total is approximately 11.2-12.2%. The weight ratio of polyester non-microdenier stretchable yarn (used in the warp) to yarn in total is 27-33%.

The polyester knit fabric backing obtained is conditioned in the oven for thermal shrinkage.

The sample of the fabric has been subjected to the wicking test. The fragment of backing having included 9 warp yarn threads (1.9-2.3 cm) and of the length 8-9 cm is folded into loop of 1.75-2.25 diameter. The wetting liquid is polypropylene glycol (Desmophen 2061BD). The wetted surface is 1 mm below the medium surface. The wetting level has been evaluated after 10 min using a Thermo Khan Radian DCA 322 Tensiometer. For the several samples tested an average value of 413 g has been obtained.

The fabric samples of Example 1 were coated with the standard ESCP resin to the required level of resin content (e.g. 55%, 60%, 65%). The samples were stored at 50° C. and were inspected following 2 weeks and 4 weeks. No pooling occurs on ageing of resin-coated fabric on any of resin content tested.

The fabric samples were subjected to the delamination test. This test measures the force necessary to delaminate a cured cylindrical ring of a resin-coated material. Each cylindrical ring includes 6 layers of the resin-coated material having an inner diameter of 5.1 cm. The width of the ring formed was the same as the width of the resin-coated material employed. The final calculation of the delamination strength is given in terms of newtons per centimeter of tape width.

Delamination Test Method.

Each cylindrical ring is formed by taking a roll of the resin-coated material from its storage pouch and immersing the roll completely in deionized water having a temperature of about 27° C. for about 30 seconds. The roll of resin-coated material is then removed from the water and the material is wrapped around a 5.1 cm mandrel covered with a thin stockinet (such as 3M Synthetic Stockinet MS02) to form 6 complete uniform layers using a controlled wrapping tension of about 45 grams per centimeter width of the material. A free tail of about 15.24 cm is kept. Each cylinder is completely wound within 30 seconds after its removal from the water.

The delamination strength is determined after 10 and after 30 minutes from the initial immersion in water. The free tail of the cylindrical sample is placed in the jaws of the testing machine (e.g. Instron Model 1122 machine) and a spindle is positioned through the hollow core of the cylinder to allow free rotation about the axis of the spindle. The Instron machine was then activated to pull on the free tail of the sample at a speed of about 127 cm/min.

The average force required to delaminate the wrapped layers over the first centimeters of the cylinder is then recorded in terms of force per unit width of sample (newtons/cm). For each material 5 samples of different width (5.08, 7.62, 10.16 and 12.7 cm) were tested, and the average delamination force was then calculated and reported as the delamination strength.

The test results for the resin-coated fabric of resin content 60% (more specifically 60±2%) are presented in Table 2 (10 min test) and Table 3 (30 min test). The test results for the resin-coated fabric of resin content 65% (more specifically 65±2%) are presented in Table 4 (10 min test) and Table 5 (30 min test). For each sample a specific resin content level is determined (presented in the columns on the right, respectively).

TABLE 2

Delamination strength 10 min test for the fabric of resin content 60 ± 2%
Fabric width [cm]

| 5.08 | 7.62 | 10.16 | 12.7 | 5.08 | 7.62 | 10.16 | 12.7 |
|---|---|---|---|---|---|---|---|
| Delamination strength [N/cm] | | | | Resin content [%] | | | |
| 1.23 | 3.10 | 1.73 | 2.64 | 58.27 | 60.43 | 58.82 | 58.67 |
| 2.03 | 2.98 | 1.91 | 2.26 | 60.18 | 61.32 | 60.48 | 58.64 |
| 2.61 | 2.89 | 2.31 | 2.03 | 61.06 | 61.19 | 61.07 | 59.22 |
| 2.31 | 3.01 | 2.17 | 2.15 | 60.81 | 61.5 | 60.13 | 59.08 |
| 0.96 | 3.17 | 2.19 | 2.05 | 58.23 | 61.82 | 60.49 | 59.17 |
| Average delamination strength [N/cm] | | | | Average resin content [%] | | | |
| 1.83 | 3.03 | 2.06 | 2.23 | 59.71 | 61.25 | 60.20 | 58.96 |

TABLE 3

Delamination strength 30 min test for the fabric of resin content 60 ± 2%
Fabric width [cm]

| 5.08 | 7.62 | 10.16 | 12.7 | 5.08 | 7.62 | 10.16 | 12.7 |
|---|---|---|---|---|---|---|---|
| Delamination strength [N/cm] | | | | Resin content [%] | | | |
| 2.08 | 2.73 | 3.49 | 3.52 | 60.51 | 60.23 | 60.81 | 59.75 |
| 1.94 | 3.24 | 2.73 | 2.63 | 60.46 | 61.04 | 61.05 | 59.25 |
| 2.36 | 2.73 | 3.38 | 2.80 | 59.53 | 61.72 | 61.29 | 60.98 |
| 2.94 | 4.96 | 2.14 | 2.52 | 60.49 | 61.97 | 61.19 | 59.1 |
| 2.26 | 3.71 | 2.80 | 2.84 | 60.23 | 61.32 | 59.81 | 59.37 |
| Average delamination strength [N/cm] | | | | Average resin content [%] | | | |
| 2.32 | 3.47 | 2.91 | 2.86 | 60.24 | 61.26 | 60.83 | 59.69 |

TABLE 4

Delamination strength 10 min test for the fabric of resin content 65 ± 2%
Fabric width [cm]

| 5.08 | 7.62 | 10.16 | 12.7 | 5.08 | 7.62 | 10.16 | 12.7 |
|---|---|---|---|---|---|---|---|
| Delamination strength [N/cm] | | | | Resin content [%] | | | |
| 5.27 | 5.57 | 5.97 | 5.03 | 64.69 | 65.11 | 64.55 | 64.14 |
| 5.08 | 6.76 | 4.80 | 5.60 | 63.45 | 65.51 | 64.59 | 64.46 |
| 4.82 | 5.39 | 5.50 | 5.15 | 64.46 | 63.97 | 64.64 | 63.25 |
| 3.49 | 5.29 | 5.55 | 4.47 | 63.98 | 63.95 | 64.89 | 63.55 |
| 4.99 | 5.29 | 5.13 | 4.12 | 64.27 | 64.02 | 64.26 | 64.26 |
| Average delamination strength [N/cm] | | | | Average resin content [%] | | | |
| 4.73 | 5.66 | 5.39 | 4.87 | 64.17 | 64.51 | 64.59 | 63.93 |

TABLE 5

Delamination strength 30 min test for the fabric of resin content 65 ± 2%
Fabric width [cm]

| 5.08 | 7.62 | 10.16 | 12.7 | 5.08 | 7.62 | 10.16 | 12.7 |
|---|---|---|---|---|---|---|---|
| Delamination strength [N/cm] | | | | Resin content [%] | | | |
| 8.60 | 9.18 | 8.67 | 5.90 | 65.18 | 65.02 | 64.76 | 64.03 |
| 8.28 | 9.84 | 7.51 | 6.34 | 65.07 | 65.65 | 64.47 | 64.37 |
| 8.42 | 10.21 | 7.76 | 8.93 | 64.09 | 65.74 | 63.37 | 65.26 |
| 7.71 | 8.25 | 7.86 | 7.29 | 64.93 | 65.46 | 64.2 | 64.16 |
| 5.06 | 5.88 | 6.67 | 5.04 | 63.46 | 63.06 | 64.61 | 63.69 |
| Average delamination strength [N/cm] | | | | Average resin content [%] | | | |
| 7.61 | 8.67 | 7.70 | 6.70 | 64.55 | 64.99 | 64.28 | 64.30 |

The results indicate, that the exemplary fabric exhibits good lamination properties.

Water vapor permeability test (MVTR) has been performed according to the MVTR-LYSSY method, i.e. with the use of the water vapor permeability tester "Lyssy" having air pump "L80-5000". The results of MVTR measurements for the fabric impregnated with cured resin are presented in Table 6.

TABLE 6

| | Resin content | | | |
|---|---|---|---|---|
| | 60.56% | 60.74% | 59.91% | 59.83% |
| MVTR g/m²/24 h | 1811 | 1760 | 1823 | 1870 |
| | Resin content | | | |
| | 64.9% | 64.86% | 64.21% | 63.81% |
| MVTR g/m²/24 h | 1862 | 1892 | 1889 | 1900 |

The results of the test proves that the use of fabric according to invention to form an orthopedic support material allows to form a cast of acceptable porosity, which is breathable and comfortable for the patient.

EXAMPLE 2

Polyester microdenier yarn used in weft is 167 dtex/144f/1, i.e. composed of filaments of 1.045 denier (1.16 dtex).

The multi-filament yarn is 500 dtex/96f/1—not twisted—i.e. multi-filament yarn of filaments of 4.69 denier (5.21 dtex). The yarn 500 dtex/96f/1 is the stiffness controlling yarn. The ratio of microdenier threads to multi-filament threads in the weft is 2:1. The weight ratio of microdenier yarn to multi-filament yarn in the weft yarn is approximately ca. 1:1.5. Both, microdenier yarn and multi-filament yarn are made of poly(ethylene terephthalate). The polyester microdenier yarn and polyester multi-filament yarn are air jet intermingled.

Polyester heat shrinkable, non-microdenier stretchable yarn used in the warp is 167 dtex/72f, i.e. composed of filaments of 2.09 denier (2.32 dtex). The stretchable yarn is made of poly(ethylene terephthalate) and poly(trimethylene terephthalate).

The weight ratio of polyester microdenier yarn to yarn in total is approximately 26.8-29.0%. The weight ratio of polyester non-microdenier stretchable yarn (used in the warp) to yarn in total is 27-33%.

The polyester knit backing obtained is conditioned in the oven for thermal shrinkage.

The sample of the fabric has been subjected to the wicking test. The evaluation has been performed according to the procedure described in Example 1. For the several samples tested an average value of 443 g has been obtained.

The fabric samples of Examples 2 were coated with the standard ESCP resin to the required level of resin content (e.g. 55%, 60%, 65%). The samples were stored at 50° C. and were inspected following 2 weeks and 4 weeks. No pooling occurs on ageing of resin-coated fabric on any of resin content tested.

The invention claimed is:

1. A resin-coated sheet material comprising:
   a knit fabric, said knit fabric comprising:
      a weft yarn comprising:
         a synthetic organic microdenier yarn of no greater than 1.5 denier per filament (dpf) and made of polyester, the synthetic organic microdenier yarn used in weft,
         synthetic organic multi-filament yarn of greater than 2.5 denier per filament (dpf) and up to 6 dpf and made of polyester, the synthetic organic multi-filament yarn used in weft, wherein the synthetic organic microdenier yarn and the synthetic organic multi-filament yarn are air jet intermingled to form the weft yarn,
      a synthetic organic non-microdenier stretchable yarn used in warp, and
   a curable resin coated onto the knit fabric.

2. The resin-coated sheet material according to claim 1, wherein the weight ratio of the synthetic organic microdenier yarn to yarn in total is 10-30%.

3. The resin-coated sheet material according to claim 1, wherein the synthetic organic microdenier yarn is of 0.8-1.3 dpf.

4. The resin-coated sheet material according to claim 1, wherein the synthetic organic multi-filament yarn is of 3.5-6 dpf.

5. The resin-coated sheet material according to claim 1, wherein the threads of the synthetic organic multi-filament yarn are not twisted.

6. The resin-coated sheet material according to claim 1, wherein the weight ratio of the synthetic organic microdenier yarn to the synthetic organic multi-filament yarn is between 1:1.3 to 1:6.

7. The resin-coated sheet material according to claim 1, wherein the polyester is poly(ethylene terephthalate).

8. The resin-coated sheet material according to claim 1, wherein a weight ratio of the synthetic organic non-microdenier stretchable yarn to yarn in total is 27-33%.

9. The resin-coated sheet material according to claim 1, wherein the synthetic organic non-microdenier stretchable yarn is made of polyester.

10. The resin-coated sheet material according to claim 9, wherein the polyester comprises poly(ethylene terephthalate), poly(trimethylene terephthalate) or their combinations.

11. The resin-coated sheet material according to claim 1, wherein the curable resin is a water curable resin.

12. The resin-coated sheet material according to claim 11, wherein the water curable resin is an isocyanate functional prepolymer.

* * * * *

UNITED STATES PATENT AND TRADEMARK OFFICE
CERTIFICATE OF CORRECTION

| | | |
|---|---|---|
| PATENT NO. | : 10,415,181 B2 | Page 1 of 1 |
| APPLICATION NO. | : 14/783182 | |
| DATED | : September 17, 2019 | |
| INVENTOR(S) | : Pawel A. Tomza | |

It is certified that error appears in the above-identified patent and that said Letters Patent is hereby corrected as shown below:

On the Title Page

Column 2, Item (56) Other Publications, Line 4, Delete "Fairchils" and insert -- Fairchilds --, therefor.

In the Specification

Column 3
Line 32, Delete "mulifilament" and insert -- multifilament --, therefor.

Column 7
Line 60, Delete "non-microdernier" and insert -- non-microdenier --, therefor.

Signed and Sealed this
Fifth Day of May, 2020

Andrei Iancu
*Director of the United States Patent and Trademark Office*